United States Patent [19]

Rosenthal

[11] Patent Number: 4,466,076
[45] Date of Patent: * Aug. 14, 1984

[54] APPARATUS FOR NEAR INFRARED QUANTITATIVE ANALYSIS WITH TEMPERATURE VARIATION CORRECTION

[75] Inventor: Robert D. Rosenthal, Gaithersburg, Md.

[73] Assignee: Trebor Industries, Inc., Gaithersburg, Md.

[*] Notice: The portion of the term of this patent subsequent to Sep. 20, 2000 has been disclaimed.

[21] Appl. No.: 355,325

[22] Filed: Mar. 8, 1982

Related U.S. Application Data

[63] Continuation-in-part of Ser. No. 263,881, May 15, 1981, Pat. No. 4,404,642.

[51] Int. Cl.³ .................... G06F 15/20; G01N 21/00
[52] U.S. Cl. .................................. 364/571; 364/498; 364/557; 250/338; 356/418
[58] Field of Search ...................... 364/496–499, 364/526, 557, 571; 250/338, 341, 343, 345; 356/416, 418

[56] References Cited

U.S. PATENT DOCUMENTS

| | | | |
|---|---|---|---|
| 3,776,642 | 12/1973 | Anson et al. | 364/497 |
| 3,828,173 | 8/1974 | Knepler | 364/498 |
| 4,193,116 | 3/1980 | Funk | 364/497 |
| 4,253,766 | 3/1981 | Funk | 364/526 |
| 4,260,262 | 4/1981 | Webster | 364/526 |
| 4,286,327 | 8/1981 | Rosenthal et al. | 364/497 |
| 4,404,642 | 9/1983 | Rosenthal | 364/498 |

OTHER PUBLICATIONS

"An Introduction to Near Infrared Quantitative Analysis" Presented by R. Rosenthal at the 1977 Annual Meeting of American Association of Cereal Chemist.

Primary Examiner—Gary Chin
Attorney, Agent, or Firm—Bernard, Rothwell & Brown

[57] ABSTRACT

A near infrared quantitative analysis instrument provides for correction of wide temperature variations in unground cereal grain sample and the ambient by providing thermistors to measure the temperature of the sample and the ambient and utilizing the measurements as additional variables in multiple regression equations.

8 Claims, 5 Drawing Figures

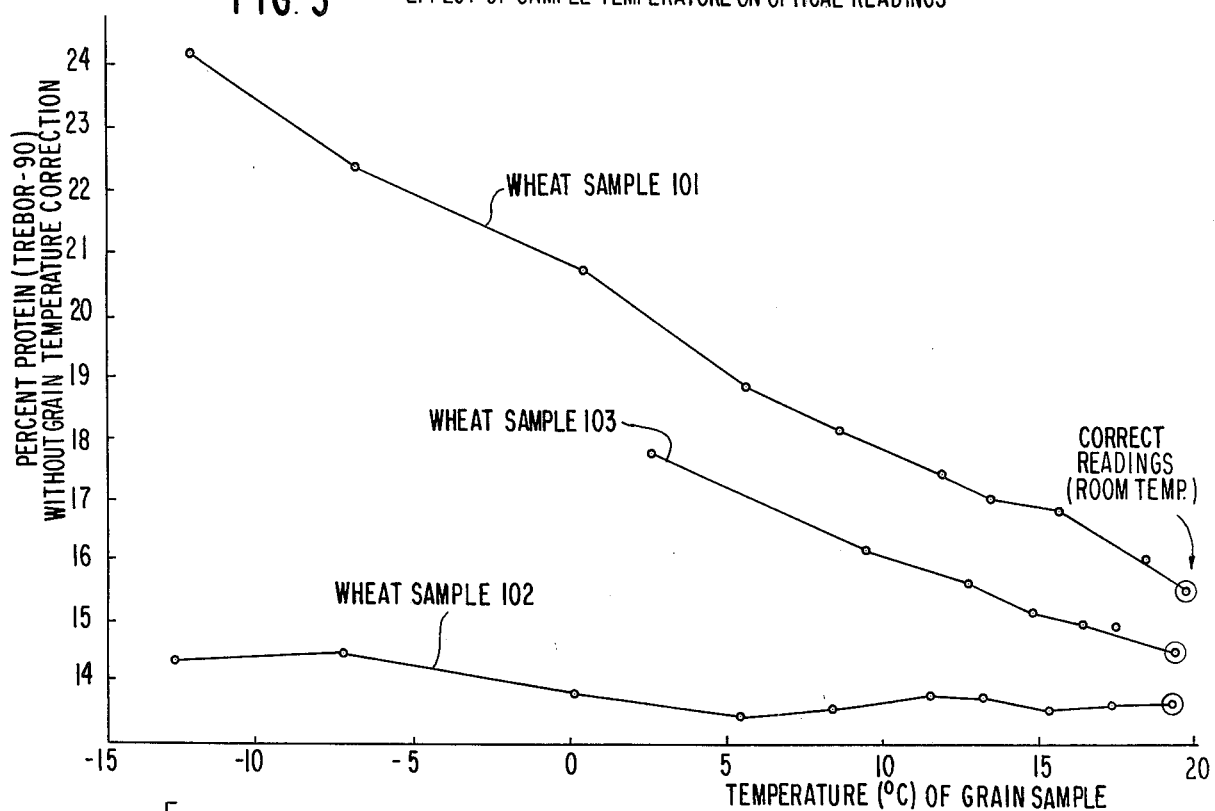
FIG. 3  EFFECT OF SAMPLE TEMPERATURE ON OPTICAL READINGS
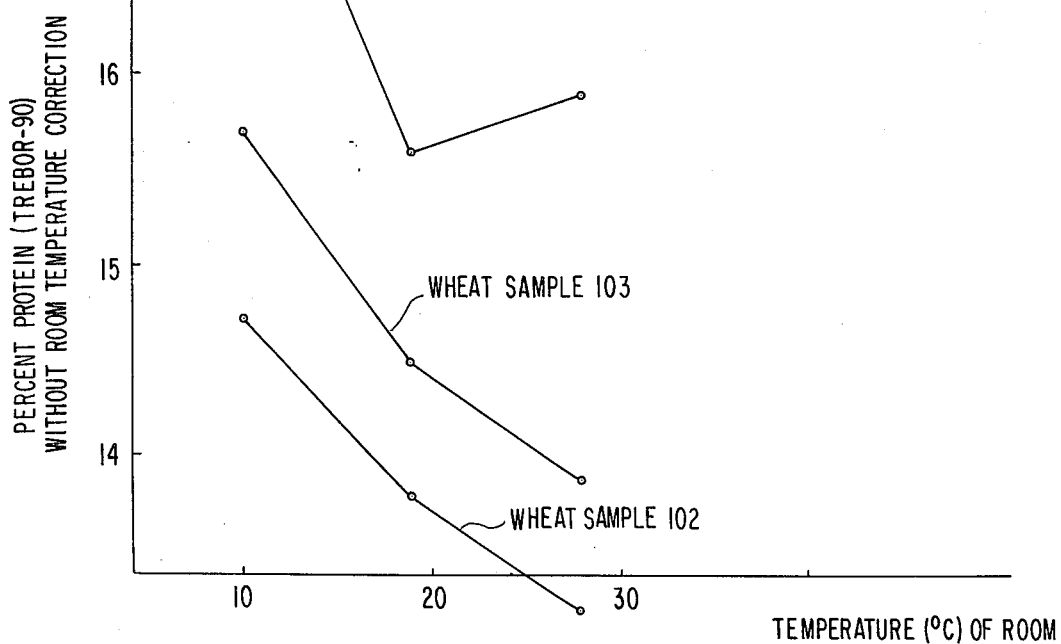
FIG. 4  EFFECT OF ROOM TEMPERATURE VARIATION ON OPTICAL READINGS

APPARATUS FOR NEAR INFRARED QUANTITATIVE ANALYSIS WITH TEMPERATURE VARIATION CORRECTION

CROSS REFERENCE TO RELATED APPLICATIONS

This application is a continuation-in-part of prior application Ser. No. 263,881 filed May 15, 1981 now U.S. Pat. No. 4,404,642.

BACKGROUND OF THE INVENTION

1. Field of the Invention

This invention relates to improvements in instruments for accomplishing near infrared quantitative analysis and particularly for improvements for correcting for wide temperature variations of both the ambient environment and the sample measured by such instruments.

2. Prior Art

Near infrared quantitative analysis instruments are known and commercially available. Such instruments known in the prior art make use of the phenomenon that certain organic substances absorb energy in the near infrared region of the spectrum. By measuring the amount of energy absorbed by the substances at specific wavelengths, precise quantitative measurements of the constituents of a product can be determined. For example, protein and moisture analysis in cereal grain can be determined by such instruments. For a general introduction to near infrared quantitative analysis, see the paper presented by Robert D. Rosenthal to the 1977 annual meeting of American Association of Cereal Chemists entitled "An Introduction to Near Infrared Quantitative Analysis".

Attention is also directed to the patent granted to Robert D. Rosenthal and Scott Rosenthal entitled "Apparatus for Near Infrared Quantitative Analysis" assigned to the assignee of this invention, U.S. Pat. No. 4,286,327 granted Aug. 25, 1981 and specifically to the prior art cited therein.

Some prior art near infrared quantative analysis instruments which measure the protein, moisture, etc., of cereal grain require the grain sample to be ground into small particles. It is highly desirable to be able to measure and analyze a sample of products without the need for grinding the sample. Grinding is time consuming, noisy and requires expensive equipment.

However, one serious problem results from attempting measurement by near infrared quantitative analysis of unground sample, especially if the sample is subject to widely varying temperature. This is due to temperature effects on the absorption wavelengths being measured. In the prior art near infrared instruments (e.g., of the reflected type) where a grinder was necessary to pulverize the sample prior to measurement, the grinding incidentally heated the sample to a constant temperature that was independent of the ambient temperature. Thus, when the ground sample was inserted into the prior art near infrared instruments, the sample was essentially at a constant temperature.

Near infrared quantitative analysis instruments are used quite often to measure the protein or moisture of grain in an out-of-doors location e.g., a grain elevator scale house and the temperature may vary from 40° F. in the winter to as high as 120° F. in the summer. This very broad temperature range will cause great inaccuracies in measurement of constituents of the products such as unground grain. This is because the moisture absorption wavelengths on which the instruments rely shift significantly with temperature and thus measurement of all the constituents (for example, protein, oil and moisture) is greatly influenced by this shift in moisture absorption peak. This adverse effect of temperature variation is true of measurements in the 1000 nm range (where measurements of this invention's commercial embodiment are made) as well as other absorption bands including the 1800–2500 nm band, where the prior art U.S. Pat. No. 3,776,642 is applicable.

It is known to provide near infrared instruments for protein analysis with internal heaters to heat its ambient to a temperature above the maximum that is expected to be encountered, e.g., such instruments normally operate at approximately 110° F. to 120° F. However, such internal heaters are expensive and wasteful of expensive power. The heat also adversly affects the reliability and life of the instruments' electronic components.

Of course measurement of the temperature of sample is a common place occurrence in laboratory instruments. Typical temperature measurement devices include thermocouples, thermopiles and other temperature measuring means that usually use the change in electrical property of a sample to measure the sample temperature. In the past, however, near infrared quantitative analysis instruments only used optical measurements. They have never previously combined more than one type of basic measurement, that is, to applicant's knowledge, the prior art never combined optical measurement with temperature measurement and linear regression correction in near infrared quantitative analysis instruments.

SUMMARY OF THE INVENTION

This invention provides for elimination of error due to wide temperature variations of a sample to be analyzed by near infrared instrumentation. It also eliminates the need for heaters, and allows operation in widely varying ambient conditions. It accomplishes these results by utilizing thermistors, one inserted into the unground product sample which provides a measurement of the sample temperature and another for measuring ambient. The output of each thermistor is then utilized as one additional variable in multiple regression equations with optical data provided by the near infrared instrument. By combining direct temperature measurement of the sample and the ambient with optical data from the infrared absorption of the sample in the multiple regression equations highly accurate measurements of protein and moisture have been achieved.

BRIEF DESCRIPTION OF THE DRAWINGS

FIG. 3 is a graph illustrating the effect of sample temperature on the optical readings.

FIG. 4 is a graph illustrating the effect of room temperature variation on the optical readings.

DETAILED DESCRIPTION OF THE PREFERRED EMBODIMENT

Figure 1:
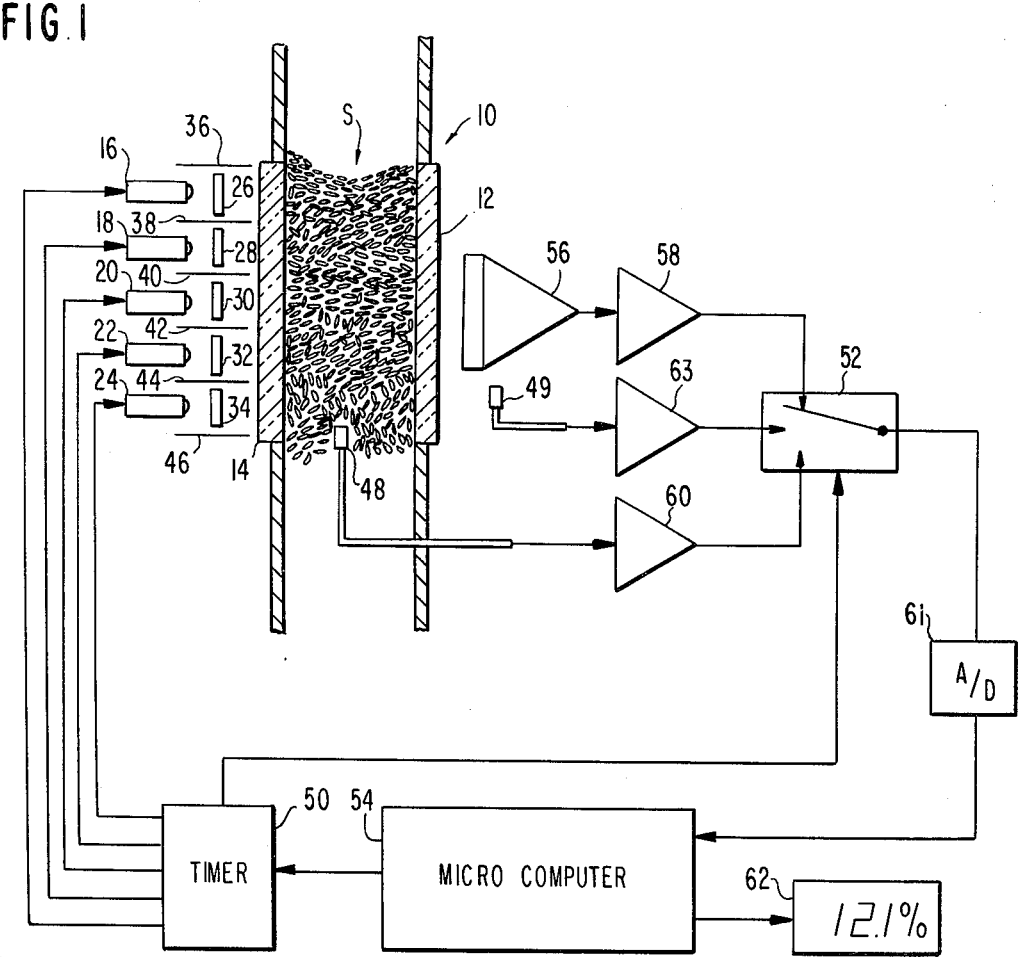
FIG. 1 is a schematic diagram of the near infrared quantitative analysis instrument of this invention including the electrical circuitry therefor.

In FIG. 1 a sample holding means 10 can be any form of suitable chamber having at least a portion thereof transparent to infrared energy such as windows 12 and 14. A sample S to be analyzed may be unground cereal grain. This sample is contained within the holding chamber 10 during the measurement. Suitable gates (not shown) are positioned to put the sample in the chamber during measurement and remove the sample from the chamber following measurement.

A plurality of infrared emitting diodes (IREDs) 16, 18, 20, 22 and 24 are positioned so that when sequentially pulsed they will emit their illumination or infrared energy through individual narrow bandpass filters 26, 28, 30, 32 and 34. Although five IREDs are shown the actual number used may be more or less than five. Suitable shields such as baffles 36, 38, 40, 42, 44 and 46 shield the individual IREDs and filters. The beams from the individual IRED's may be brought to a single spot by suitable lens means, not shown. Each narrow bandpass filter yields one of the specified wavelengths required for the quantitative analysis. For further reference as to the operation of these pulsed IREDs and narrow bandpass filters see the patent of Rosenthal et al., U.S. Pat. No. 4,286,327 granted Aug. 25, 1981.

The temperature of the sample S that is being measured is sensed by a thermistor 48 positioned within the holding chamber 10 in contact with the sample. The temperature may be sensed one or more times per IRED sequential cycle. The ambient temperature is also sensed by a thermistor 49 located within the instruments housing (not shown) and may be also sensed one or more times per IRED cycle.

A timer 50 is connected to the individual IREDs 16-24 to sequentially pulse them and the timer is also connected to a switch 52 to allow measurement of the temperature at each thermistor at least once per IRED cycle sequence. Because temperature changes slowly it is not necessary to sample it during each cycle. The timer itself is controlled from a micro computer 54.

The optical energy transmitted through the sample S by each of sequenced IREDs is quantitatively detected by a photovoltaic sensor 56. The output of the sensor is then amplified in amplifier 58 and fed to the switch 52.

The output of the thermistors 48 and 49 are also amplified in amplifiers 60 and 61 and fed to the switch 52. The circuit from the switch 52 to the microcomputer 54 includes an analog-to-digital converter 61 to convert the signal to digital form for entry into the micro computer 54.

Figure 2:
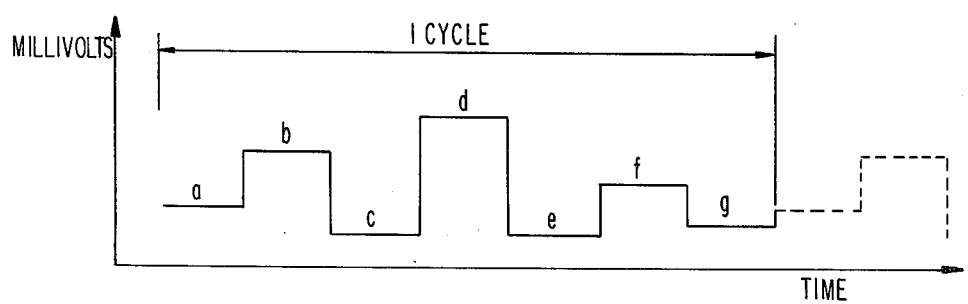
FIG. 2 is a diagram of the combined signal from the thermistor and optical sensor for one cycle of operation.

FIG. 2 shows a cycle of signals which are fed to the micro computer. Pulses a, b, c, d and e are those read by the photovoltaic sensor 56 as a result of the infrared energy from each of the pulsed IREDs transmitted through the narrow bandpass filters which is not absorbed by the sample. The output of thermistor 48 is pulse f and the output of thermistor 49 is pulse g. This cycle of pulses shown in FIG. 2 is accomplished by causing switch 52 to obtain the temperature reading of the sample and the ambient once each cycle. The micro computer 54 combines the data with previously derived regression co-efficient to provide quantitative results, i.e., percent protein on a digital display 62.

The formula for determining percent protein in cereal grain in a typical near infrared instrument without temperature connection is as follows.

(1). $\% \text{ protein} = k_o + K_1(OD)_1 + K_2(OD)_2 + \ldots + K_n(OD)_n$, where $k_0, k_1, \ldots k_n$ are proportionality constants derived by multiple regression techniques, and $(OD)_1, (OD)_2, \ldots (OD)_n$ are optical absorption data.

However, using the present invention with temperature measurements for compensation, the following equation is utilized.

(2). $\% \text{ protein} = k'_0 + k'_1(OD)_1 + k'_2(OD)_2 + \ldots k'_n(OD)_n + k_t T + k'_t T'$. Where OD's are the optical absorption data as in equation (1); T = the grain sample temperature; T' = the ambient temperature and $k'_0 + k'_1 + k'_2 \ldots k'_n$, and $k_t$ and $k'_t$ are new multiple regression constants.

FIG. 3 is a graph showing the effect of sample temperature on optical readings utilizing a Trebor-90 instrument without grain temperature correction. The percent protein is plotted against the temperature in degrees C. of the grain sample for three separate samples. The correct readings are shown at the right hand side of the graph which is approximately room temperature. Note the variations in certain samples, particularly the wheat sample -101, as the temperature drops.

FIG. 4 is a graph showing the effect of room temperature variations on the optical readings utilizing a Trebor-90 instrument with no room temperature correction. The three grain samples of FIG. 3 were also used in the graph of FIG. 4. Note the large variations in optical readings as temperature changes, again particularly in sample 101.

Figure 5:
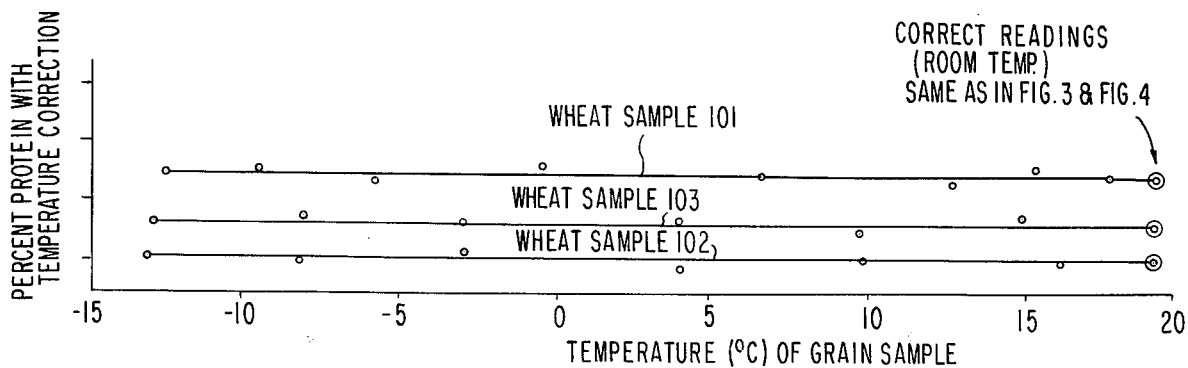
FIG. 5 is a graph showing the effect of the temperature correction utilizing this invention.

FIG. 5 is a graph similar to FIG. 3 using this invention including the equation above and the commercial Trebor-90 instrument incorporating the temperature correction of this invention. Note that for all three samples, even with a substantial variation in temperature, the readings are constant and correct.

As a nonlimiting example of the components utilized to construct this invention, the IREDs are commercially available from G.E. as IN6264. The timer 50 is National Semiconductor NE555. The photodetector 56 is Silicon Detector Corporation SD444-11-21-251. The switch 52 is Harris Corporation HI1-5050. The amplifier 60 is National Semiconductor LF355, the analog-to-digital converter 61 is from Analog Devices Corporation AD574KD, the micro computer 54 is an Intel 8085A system, and the thermistors 48 and 50 are Sierracin/Western Thermistors 1M100-2C3.

I claim:

1. An apparatus for near infrared quantitative analysis providing for correcting wide temperature variations of sample, the apparatus comprising:
   (a) means for holding a sample to be analyzed including at least a portion of a wall thereof being transparent to infrared energy,
   (b) means to transmit infrared energy toward a sample in the holding means,
   (c) a plurality of narrow bandpass filters between the means to transmit infrared energy and the sample holding means to produce desired wavelengths required for quantitative analysis,
   (d) sensor means positioned to receive and sense infrared energy transmitted through a sample to be analyzed contained in the holding means, said sensor means producing a signal related to the infrared energy received thereby,
   (e) sample temperature measuring means positioned in the sample holding means to measure the temperature of a sample therein and to produce a signal related thereto, (f) computer means for receiving the signals from the sensor means and sample temperature measuring means and combining them in multiple regression equations to compensate for variations in sample temperature, and (g) means for reading out the results of the analysis from the computer means.

2. An apparatus as in claim 1 further comprising ambient temperature measuring means positioned outside of the sample holding means to measure the temperature of the ambient and to produce a signal related thereto, and wherein the computer means also requires signals from ambient temperature measuring means and combines them into multiple regression equations to also compensate for variations in ambient temperature.

3. An apparatus as in claim 2 wherein the means to transmit infrared energy toward a sample comprises a plurality of sequentially pulsed infrared emitting diodes (IRED's).

4. An apparatus as in claim 3 further comprising; switch means in a circuit between the output of the sensor means and the sample temperature measuring means and the ambient temperature measuring means and before the computer means for providing a signal to the computer from both temperature measuring means and the sensor means during a cycle of the pulse IREDs.

5. An apparatus as in claim 4 wherein both the sample temperature measuring means and the ambient temperature measuring means are thermistors.

6. An apparatus as defined in claim 5 further comprising a timer for controlling the switch and the pulsing of the IREDs to provide for a cycle including a readout from the IREDs and the thermistors.

7. An apparatus as defined in claim 6 wherein the read out means includes a digital display operated by the computer in response to the result of solving the multiple regression equations.

8. An apparatus as defined in claim 7 wherein the sample is an unground cereal grain.

* * * * *

UNITED STATES PATENT AND TRADEMARK OFFICE
CERTIFICATE OF CORRECTION

PATENT NO. : 4,466,076
DATED : August 14, 1984
INVENTOR(S) : Robert D. Rosenthal It is certified that error appears in the above-identified patent and that said Letters Patent is hereby corrected as shown below:

At [*] Notice in the first Column of the title page, second line, delete "Sep. 20, 2000" and substitute therefor -- Sep. 13, 2000 --.

Signed and Sealed this

Twelfth Day of March 1985

[SEAL]

*Attest:*

DONALD J. QUIGG

*Attesting Officer*     Acting Commissioner of Patents and Trademarks